United States Patent [19]

Richards et al.

[11] Patent Number: 4,821,942
[45] Date of Patent: Apr. 18, 1989

[54] DRIVER FOR SURGICAL MICROSTAPLER

[75] Inventors: William D. Richards, Medway; Richard A. Clark, Holliston; John C. Meade, Walpole, all of Mass.

[73] Assignee: Ophthalmic Ventures Limited Partnership, Norwood, Mass.

[21] Appl. No.: 217,554

[22] Filed: Jul. 11, 1988

Related U.S. Application Data

[63] Continuation of Ser. No. 906,150, Sep. 11, 1986, abandoned.

[51] Int. Cl.⁴ .................................................. B25C 5/00
[52] U.S. Cl. ..................................... 227/132; 227/146; 227/19; 128/334 R
[58] Field of Search .................. 227/19, 129, 132, 146, 227/147; 128/334 R; 173/119; 42/1.08, 1.12, 1.16; 89/1.14

[56] References Cited

U.S. PATENT DOCUMENTS

| 3,753,524 | 8/1973 | Heyward | 227/132 |
| 3,949,924 | 4/1976 | Green | 227/19 |
| 4,196,836 | 4/1980 | Becht | 227/19 |
| 4,682,412 | 7/1987 | Pfeffer | 227/132 X |

FOREIGN PATENT DOCUMENTS 1353738  9/1964  France ................................ 227/132

Primary Examiner—Frank T. Yost
Assistant Examiner—James L. Wolfe
Attorney, Agent, or Firm—Schiller, Pandiscio & Kusmer

[57] ABSTRACT

The driver is disclosed for a surgical micro-suturing stapling system which does not require the use of a staple bending anvil that must be retracted after the staple is implanted. The surgical microstapler system utilizes a unique stapler head comprising a staple magazine having a series of staples attached to and supported by a surrounding frame, apparatus for advancing the staple magazine so as to position its leading staple in a predetermined dispensing position, and staple driving apparatus for implanting the leading staple into the tissue through the ejection slot. The stapler head is adapted to be connected to the driver which provides the driving force required to cause the staple driving apparatus to separate the leading staple from the magazine and implant it into the tissue to be sutured. The driver offers the advantage that can cause the staple driving apparatus to implant a staple at a velocity in excess of the ability of tissue to respond dynamically under the force of a staple being implanted. The driver also is manually powered, can be operated by one hand of the surgeon, has little or no recoil, is simple in operation, and is readily attached to or detached from the stapler head.

14 Claims, 10 Drawing Sheets

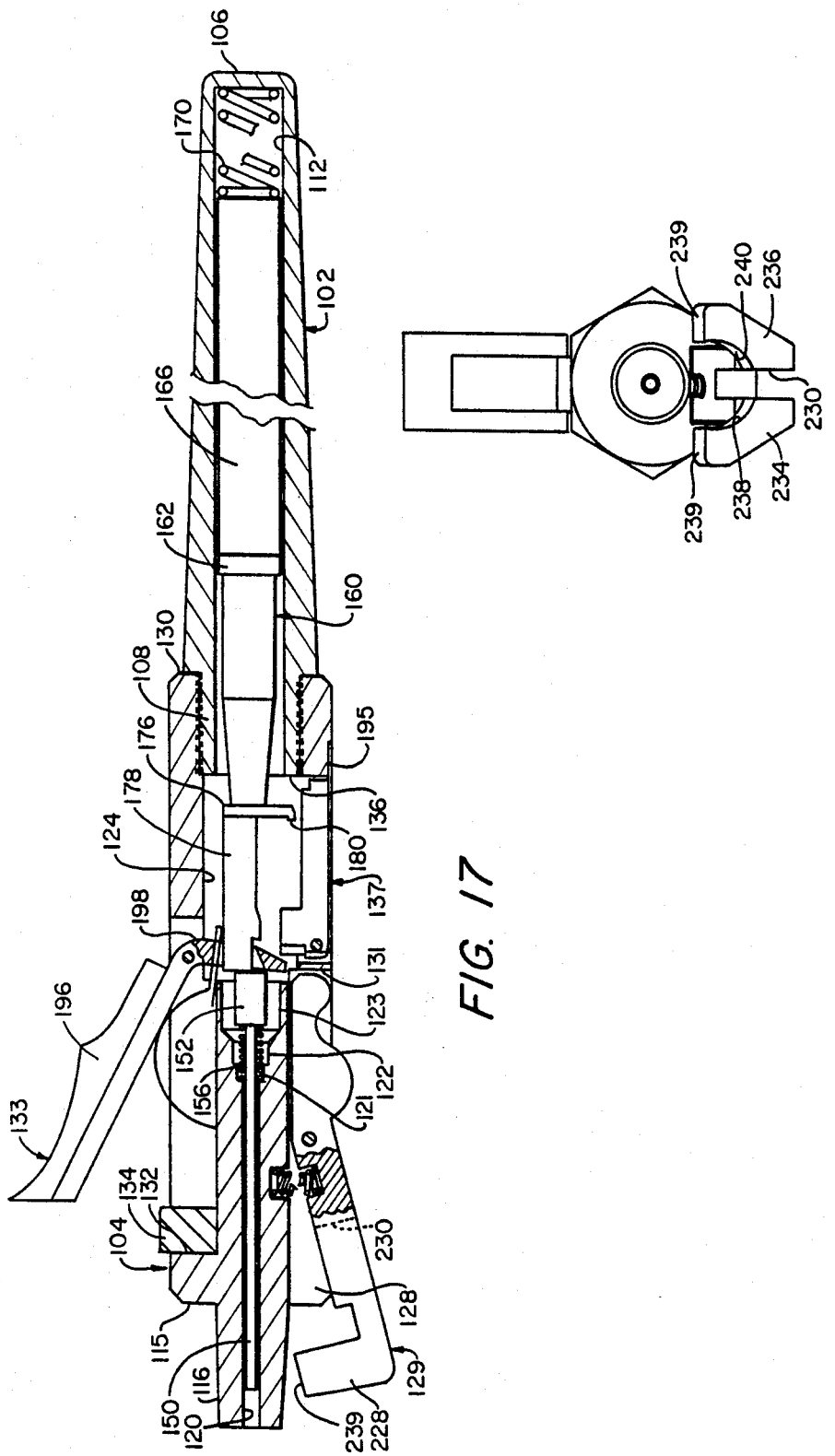

DRIVER FOR SURGICAL MICROSTAPLER

This is a continuation of application Ser. No. 906,150, filed Sept. 11, 1986, and now abandoned.

FIELD OF THE INVENTION

This invention relates to new and improved apparatus for use in suturing delicate tissue by means of fine wire staples.

BACKGROUND OF THE INVENTION

Suturing may be a very time-consuming phase of certain surgical operations, such as those involving sensitive or delicate tissue. Heretofore it has been realized that the suturing phase of many surgical operations may be shortened considerably by the use of suitable stapling devices. As a consequence a number of different types of surgical stapling devices have come into use. Some of the developments in surgical stapling devices are illustrated by U.S. Pat. Nos. 3,604,561, 3,646,801, 4,162,678, 4,316,468, 4,317,451 and 4,485,816, and the references cited therein.

However, prior surgical stapling systems suffer from one or more disadvantages, such as but not limited to: (1) excessive size of the stapler and/or staples for the intended use; (2) the need to bend the staples around an anvil as they are being implanted, which tends to induce severe traumatic effects in the tissue being sutured stemming from the need to extract the anvil from the tissue surface each time a staple has been implanted; and (3) inability to maintain precise edge alignment and smoothness as required in ophthalmic and cosmetic surgery. As a consequence, prior medical staplers have been unsuitable for uses such as delicate ophthalmic surgery where only an absolute minimum of trauma induced during the surgical procedure may be tolerated.

In an effort to avoid those or other limitations, a stapling system has been designed which consists of a stapler head that comprises (1) a staple magazine formed from a stainless steel sheet and consisting of a plurality of identical staples attached to and supported by a plurality of integral frame members, (2) means defining a staple ejection slot or aperture, (3) means for supporting the staple magazine, (4) means for advancing the staple magazine so that its leading staple is located in a predetermined dispensing position in proximity to the staple ejection slot, and (5) staple driving means having a reciprocal ram plate for severing the leading staple and driving it through the ejection slot so as to implant it into tissue engaged by the stapler head. The stapler head has no anvil, but instead the ram plate and staples are so shaped that when the ram plate is driven through its work stroke in driving engagement with the leading staple, the ram plate causes the shape of the leading staple to be transformed as it is being implanted, so that the two legs of the staple penetrate the tissue via an arc of trajectory that closely resembles the motion of a surgeon's suturing needle. The stapler head is adapted to be attached to a suitable driver which provides the force required to cause the ram plate to implant the leading staple into tissue. Such an improved stapler system is disclosed in a copending U.S. patent application filed by William D. Richards, Ernesto E. Blanco, Richard A. Clark and John C. Meade for SURGICAL MICROSTAPLER U.S. Pat. No. 217,554.

One of the major requirements of a driver suitable for use with the stapler head described in said copending U.S. patent application of William D. Richards, Ernesto E. Blanco, Richard A. Clark and John C. Meade is that it must be capable of causing the ram plate to drive the staples with a velocity which exceeds the ability of live tissue to react dynamically under the force of a penetrating staple, so as to make it unnecessary to hold the limp edges of some delicate tissues at the time of stapling. A further primary requirement is that the driver be small enough to be easily grasped and manipulated by the surgeon's hand. Another requirement is that the driver be low in weight so as to facilitate placing the stapler head in light contact with the tissue to be sutured, and also to increase operator control and lessen operator fatigue. A further requirement is that the driver be easily attached to and detached from the stapling head, so as to permit substitution of a new full stapler head when the staple head currently in use has been exhausted of staples. It also is desirable, though not essential, that the driver be manually powered, so as to eliminate the need for any electrical, hydraulic or pneumatic power cables.

Accordingly the primary object of this invention is to provide a driver for a surgical microstapler that meets the foregoing requirements.

A further object is to provide a driver that has a relatively simple construction yet provides a precise driving action on operator command.

Still other objects and advantages will be obvious to persons skilled in the art from the following detailed description which is to be considered together with the accompanying drawings.

DRAWINGS

FIG. 7 is an enlarged longitudinal sectional view of the driver shown in FIG. 1;

FIG. 18 is an end view of the same driver;

PREFERRED EMBODIMENT OF THE INVENTION

Figure 1:
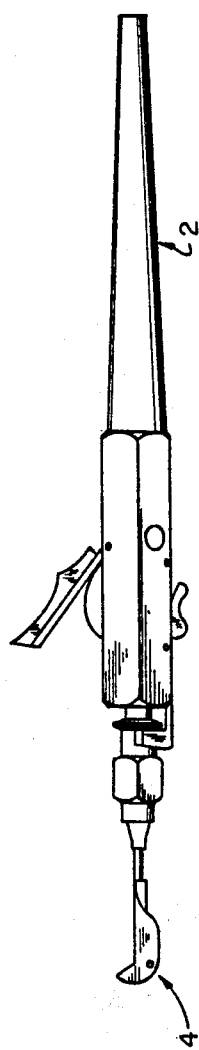
FIG. 1 is a side view in elevation of a stapling head made in accordance with this invention, in combination with a preferred driver.

Referring now to FIGS. 1-7, there is shown a microsurgical stapling system comprising a manually operable driver 2 and a stapling tool or head 4 made in accordance with the present invention. Stapling head 4 comprises a tubular stem 6, a hollow housing 8 which contains most of the critical functioning parts of the head, and a curved laminar or leaf spring 10 for advancing a staple magazine 12 (FIG. 3) into position for dispensing the leading staple through an ejection slot formed in the bottom side of hollow housing 8.

As shown in FIGS. 1-7, hollow housing 8 is formed with a curved bottom wall 14 and opposite side walls 16 and 18, with those walls converging at the rear end of the hollow body to form a circularly-shaped channel section 20 that embraces and is welded or otherwise fastened to stem 6. A staple ejection slot 22 (FIG. 4) is formed in bottom wall 14. Hollow housing 8 also is provided with an internal bulkhead 24 that is attached to side walls 16 and 18 and terminates short of bottom wall 14.

Figure 2:
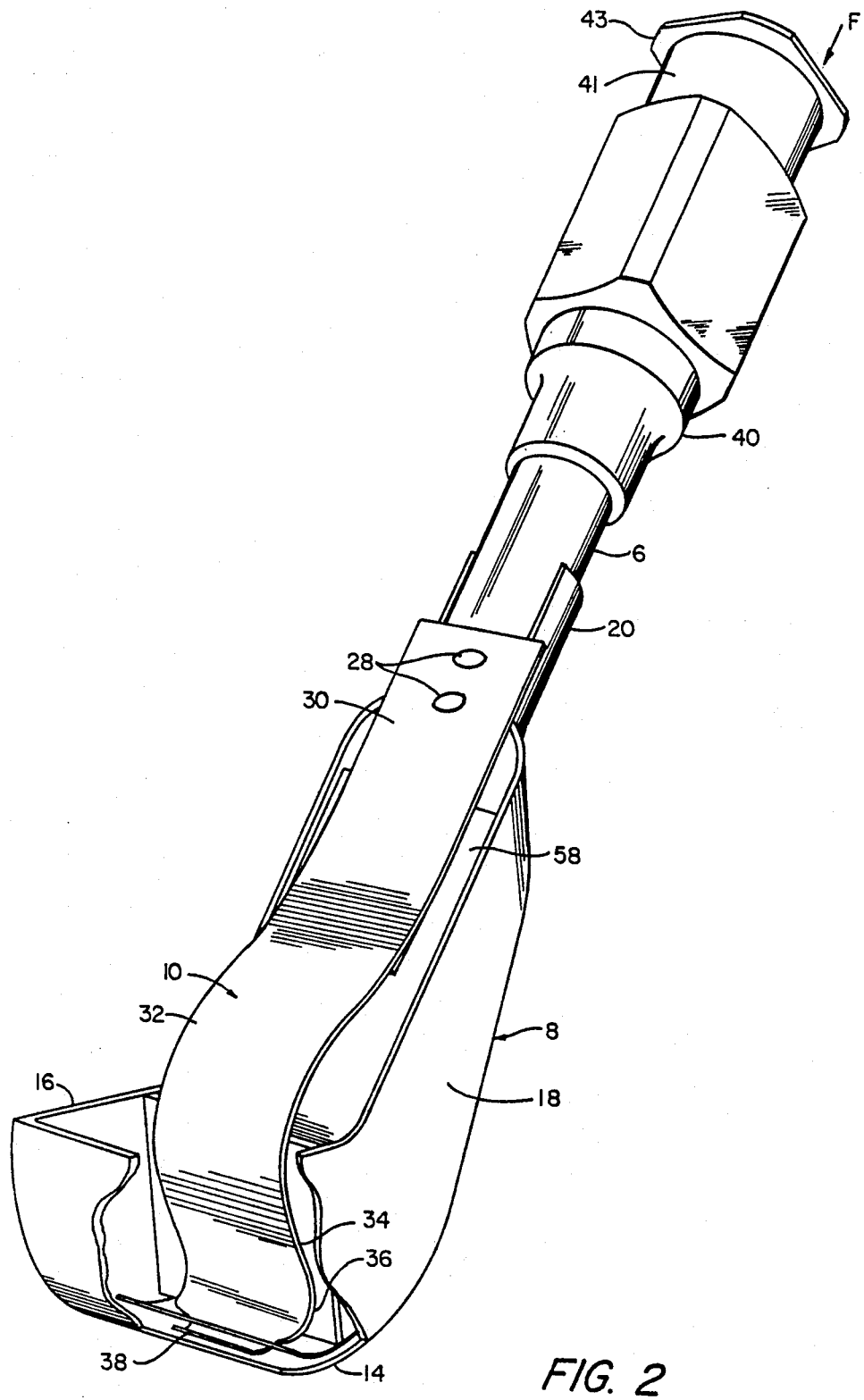
FIG. 2 is an enlarged perspective view of the same stapling heads.
Figure 5:
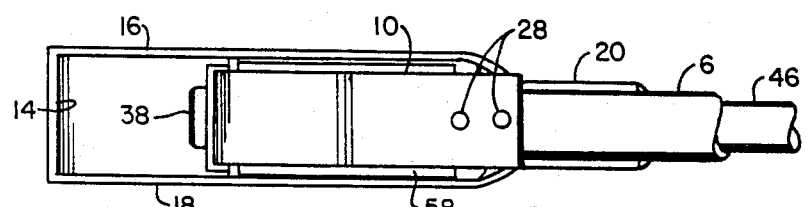
FIG. 5 is a plan view of the stapler head.
Figure 6:
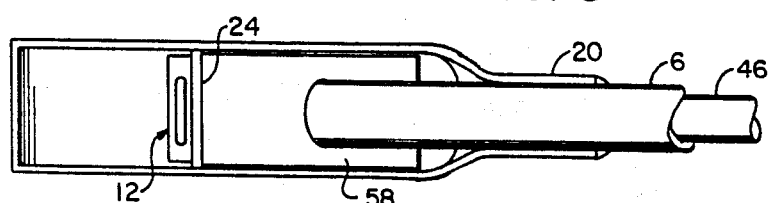
FIG. 6 is a plan view of the stapler head with the magazine feed spring member removed.
Figure 7:
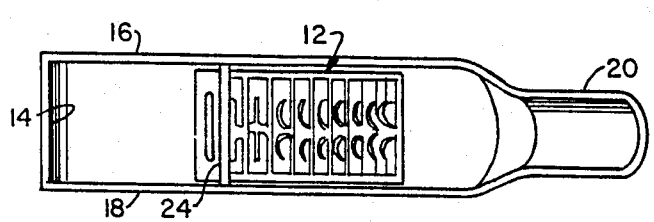
FIG. 7 is a further plan view of the stapler head with additional elements removed.

Preferably laminar spring 10 is attached to the hollow stem 6 through spot welds 28 (FIGS. 2 and 5). Spring 10 has an S-shaped curvature, comprising a relatively flat portion 30 which lies against the hollow stem 6, a convexly curved section 32 which curves away from the hollow housing 8, a nearly flat section 34 which extends down toward ejection slot 22, and a concavely curved section 36 which turns upwardly along bottom wall 14. The forward end of spring 10 is reduced in width to form a tang 38 which engages and moves the staple magazine 12 as hereinafter described.

Referring to FIGS. 1 and 2, hollow stem 6 has a hollow socket-like member 40 attached to its upper or outer end. The exterior of member 40 has a reduced diameter as shown at 41, resulting in a flange 43. The socket-like member 40 has a cylindrical axially-extending bore 42 which is counterbored as shown at 44. Bore 42 has the same diameter as the internal surface that defines axial bore 7 in stem 6. Slidably disposed within bores 7 and 42 is a plunger in the form of a ramrod 46. Adjacent its upper end the ramrod has a circular peripheral flange 48 sized to make a close sliding fit in counterbore 44. Captivated between flange 48 and the tapered bottom end 50 of counterbore 44 is a return coil spring 52. Spring 52 is a compression spring and acts to urge ramrod 46 in an upward direction, as viewed in FIG. 3.

Attached to socket-like member 40 is driver 2 for applying a driving force F (see FIGS. 2 and 3) to ramrod 46 against the force of return spring 52.

Figure 3:
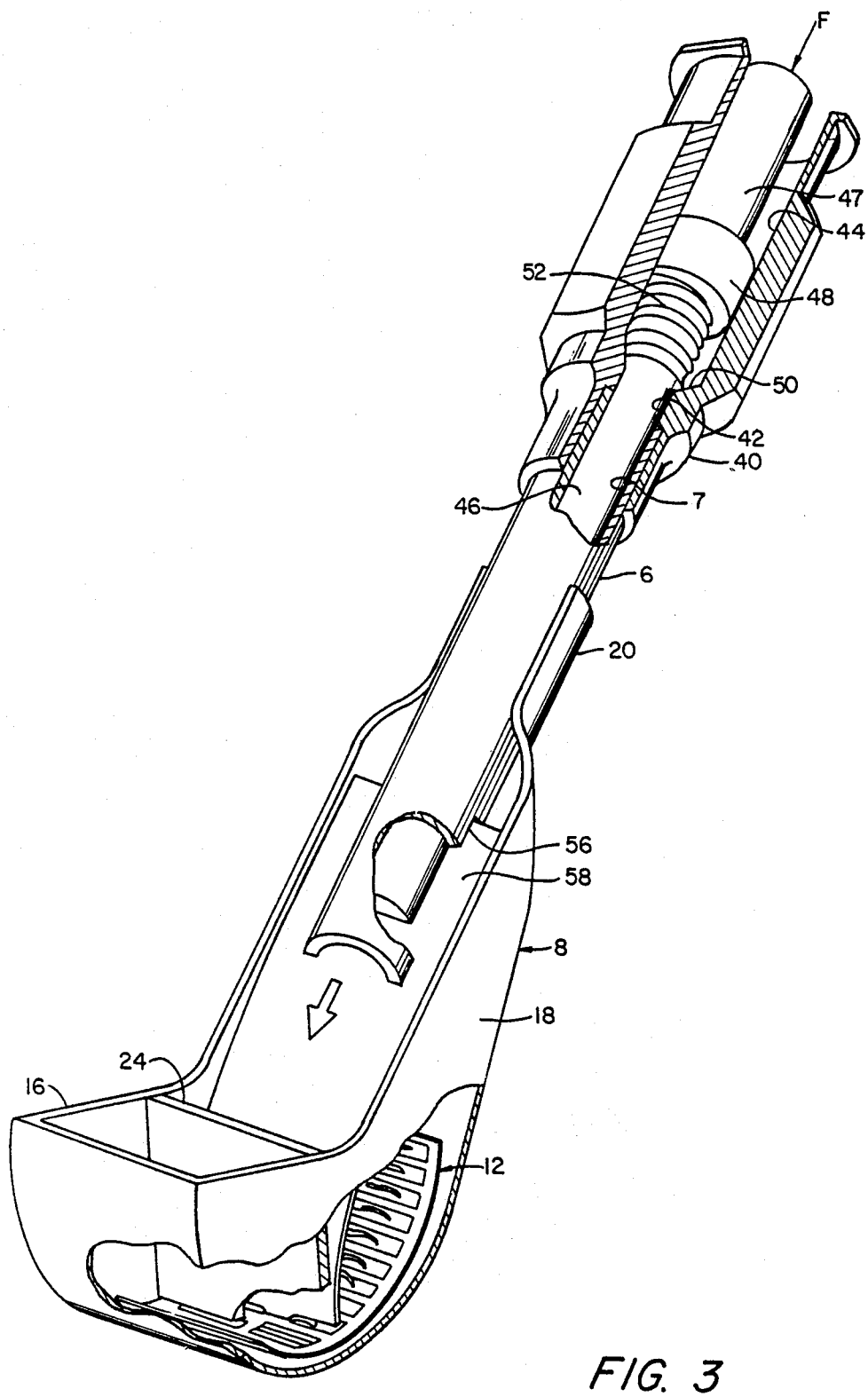
FIG. 3 is a view similar to FIG. 2, but with certain portions broken away, illustrating the disposition of staple magazine within the stapler head.
Figure 4:
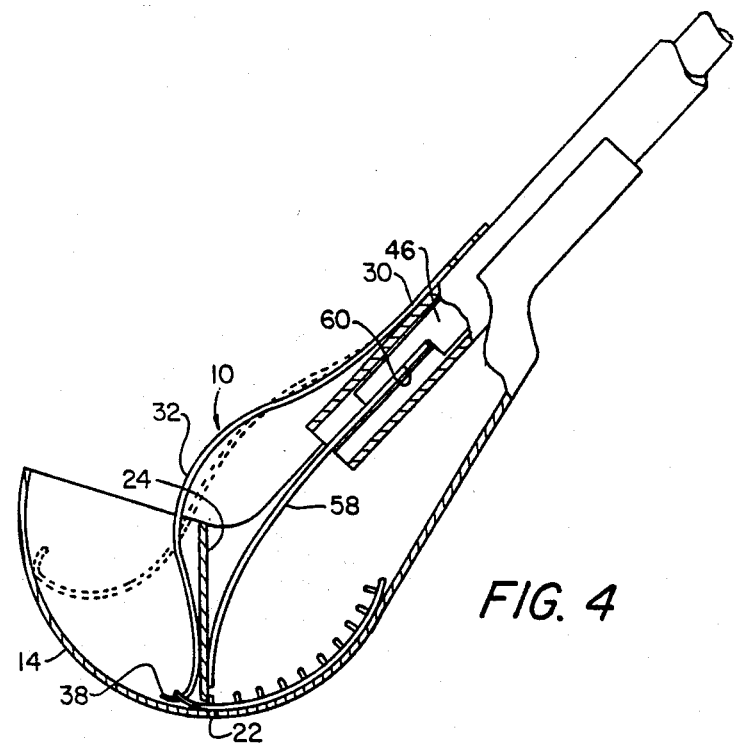
FIG. 4 is a side elevation, partly in section, illustrating disposition of the staple magazine within head.

The bottom end of hollow tubular stem 6 extends into housing 8 and is slotted along a diameter as shown at 56 (FIG. 3) to accommodate a ram plate 58 that has a curvature as shown in FIG. 4 and is secured to the bottom end of ramrod 46. For this purpose, ramrod 46 has a flat recess 60 to accommodate the upper end of ram plate 58. The latter is welded or brazed to ramrod 46. As seen in FIGS. 2 and 3, ram plate 58 is wider than the outer diameter of stem 6, so that it projects from both sides of the diametrical slot 56. With this arrangement, rectilinear axial motion of ramrod 46 and ram plate 58 relative to stem 6 is permitted, while rotational axial motion of ramrod 46 relative to stem 6 is prevented by the interaction of ram plate 58 with the portions of stem 6 that define slot 56. Also the depth of slot 56 determines the extent of rearward motion of ram plate 58, since the edge surfaces of stem 6 that determine the depth of slot 56 act as a stop for ram plate 58.

As seen best in FIGS. 3 and 4, ram plate 58 is flat where it is attached to the ramrod, but its forward half is curved downwardly. The curvature of plate 58 is set so that its forward end (the bottom end as seen in FIG. 4) extends down at substantially a right angle to bottom wall 14 of housing 8. Also the ram plate is made long enough so that its forward end is substantially parallel to and engages bulkhead 24 when the ram plate is in its retracted position (FIG. 4).

Figure 10:
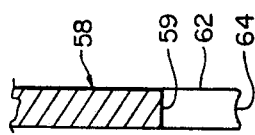
FIG. 10 is a fragmentary cross-sectional view taken along line 10—10 of FIG. 12 illustrating channels formed in the push lugs of ram plate 58.
Figure 12:
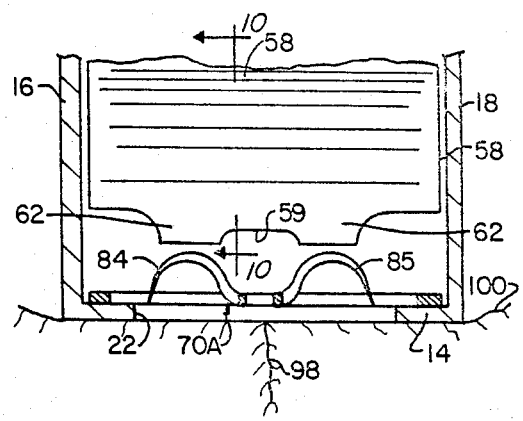
FIGS. 12, 14 and 16 are cross-sectional views, corresponding to FIGS. 11, 13 and 15 respectively, illustrating operation of the stapler head.

As seen best in FIG. 12, the bottom end of ram plate 58 is formed with two push lugs 62 that are spaced from one another. As seen in FIG. 10, the bottom edges of lugs 62 are formed with circularly-curved channels 64 to allow the lugs to conform to the shape of the top portions of the staples 70 hereinafter described. The purpose of channels 64 is to prevent the staple which is being driven from slipping out of contact with lugs 62.

Figure 9:
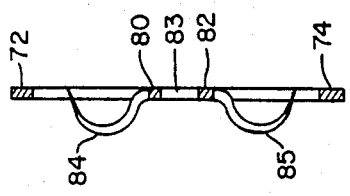
FIG. 9 is a sectional view of the staple magazine taken along line 9—9 of FIG. 8.
Figure 8:
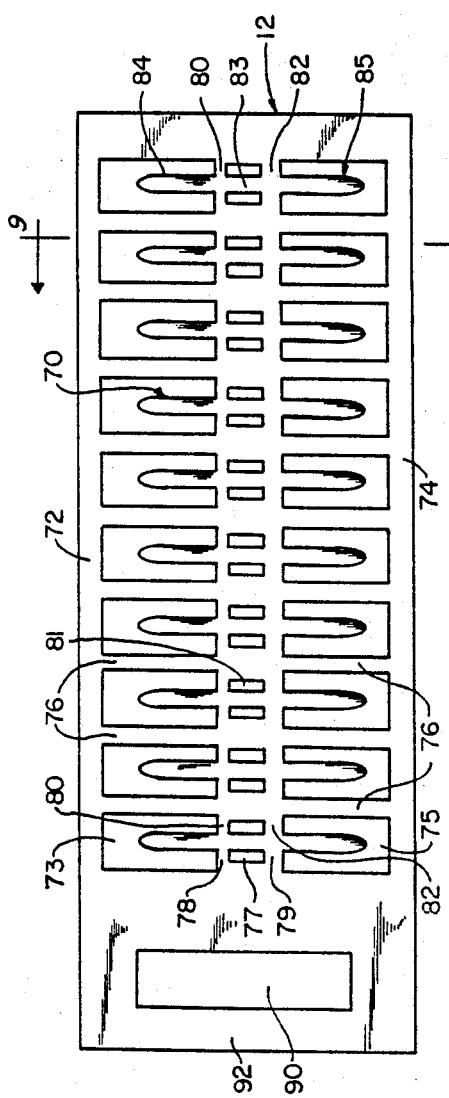
FIG. 8 is a plane view of a preferred form of staple magazine in an uncurved state.

The staple magazine 12 is formed from a flat sheet of a suitable material, preferably stainless steel, and consists of a plurality of staples 70 formed in a suitable manner, e.g. by die punching and forming. As illustrated in FIGS. 8 and 9, the staples are part of a sheet continuum, each being disposed between side frame members 72 and 74 and cross frame members 76, and each having two tiny tabs 78 and 79 on one side joining it to cross frame members 76 and two tiny tabs 80 and 82 on its opposite side joining it to cross frame members 76. As seen in FIGS. 8, 9, 12, 14 and 16, staples 70 are formed with a body or spine portion 83 and two convexly curved legs 84 and 85 that project above the plane of staple magazine 12. The legs of staples 70 are formed so that they diverge slightly from one another, e.g. each leg extends at an angle of approximately 15-20 degrees to the vertical (see FIG. 9). Magazine 12 has openings 73, 75, 77 and 81 which assist in defining staples 70, frame members 72, 74 and 76, and tabs 78, 79, 80 and 82. Additionally, each staple magazine has a leading slot 90 that receives the forward end of spring 10, plus a leading end cross-member 92 that has a greater width than the cross frame members 76, in order to provide a better force distribution in response to the staple feeding action of spring 10. Tabs 78, 79, 80 and 82 may or may not be pre-sheared to facilitate proper separation of the staples 70 from magazine 12.

The elastic force of spring 10 serves to feed the magazine toward bulkhead 24 every time that the ram plate 58 is retracted after a staple has been implanted. Each operation of ram plate 58 causes the staple magazine to be advanced a distance equal to the spacing between successive staples, with return spring 52 causing ramrod 46 to return to its original position.

As seen in FIG. 4, when the ramrod 46 is in its relaxed or raised position, the push lugs 62 of ram plate 58 are in a retracted position relative to staple magazine 12.

The mode of operation of the system is illustrated in FIGS. 11-16.

Figure 11:
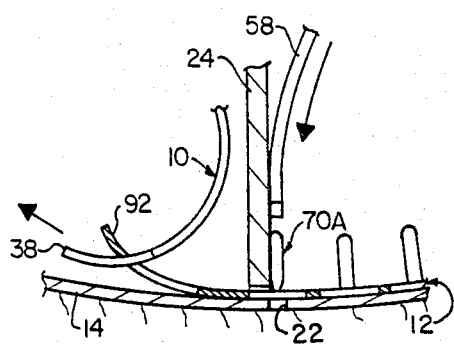
FIGS. 11, 13 and 15 are fragmentary longitudinal sectional views illustrating operation of the new stapler head under the influence of the attached driver.
Figure 13:
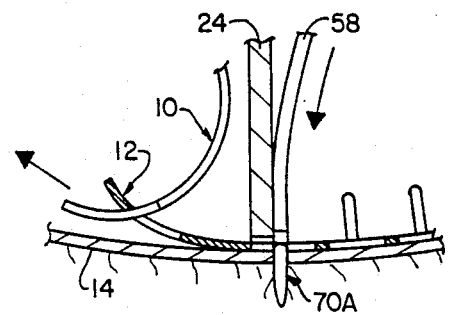
Figure 14:
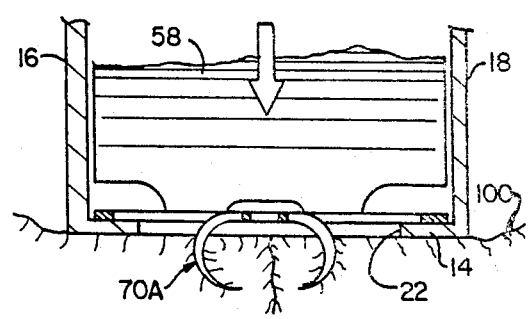
Figure 15:
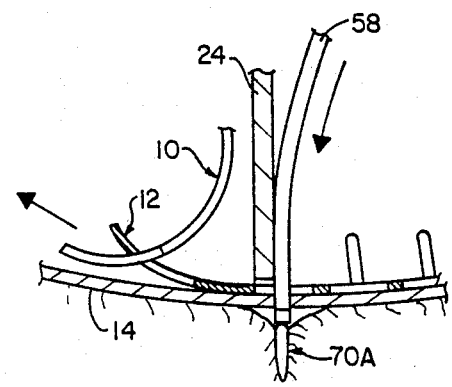
Figure 16:
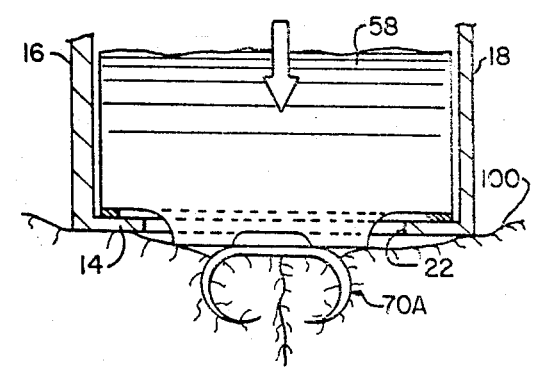

FIGS. 11, 13, and 15 provide a side view in elevation of selected elements of the system of FIGS. 1-9 in a typical surgical stapling operation, while FIGS. 12, 14, and 16 show a cross-sectional view of the same stapling operation. Referring first to FIGS. 11 and 12, the stapling head is shown positioned over an incision 98 in human tissue 100. At this time the stapling head is in its at-rest position which is characterized by the upper end of ram plate 58 being engaged with the upper end of slot 56 in stem 6 (FIG. 3) and the lower end of the same plate being engaged with bulkhead 24 but spaced from magazine 12 (FIG. 4). As seen in FIG. 12, the stapler is placed so as to straddle the incision to insure that the two legs 84 and 85 of the staple to be implanted will grasp approximately the same amount of tissue at each side of the incision. The staple to be implanted, i.e., the leading staple in the magazine, is labelled 70A in FIGS. 11-16 to differentiate it from the other staples of magazine 12. The lower end of ram plate 58 is located directly above the staple 70A that is to be implanted. Leaf spring 10 urges staple magazine 12 toward the left in FIG. 11, thereby feeding the leading staple toward the gap formed between bulkhead 24 and bottom wall 14 and holding that leading staple against the bulkhead in alignment with ejection slot 22. The staple magazine stays in this position until staple 70A is ejected, whereupon spring 10 will advance the magazine to place the next staple against the bulkhead after ram plate 58 has been retracted.

Assume that the surgeon now actuates driver 2 so as to cause ram plate 58 to be driven downwardly. As this occurs, ram plate push lugs 62 engage the upper portion of convexly curved legs 84 and 85 of staple 70A so that those portions reside in ram plate channels 64 (FIG. 10). Downward motion of ram plate 58 drives staple 70A downward so as to cause it to be sheared off from staple magazine 12. At the same time, push lugs 62 deflect the two convex legs 84 and 85 of the staple downward, with the legs following a curved trajectory as they are driven into the tissue on both sides of the incision. The engagement of channels 64 with the upper portions of legs 84 and 85 of staple 70A assures that the staple will not slide out from under ram plate lugs 62, whereby the staple is stabilized in the downward direction and prevented from squirming away from the control of ram plate 58 and its push lugs 62. The staple is guided during its downward motion by virtue of the fact that it remains engaged with bulkhead 24 until it is sheared off from its leading tabs 78 and 79 and its trailing tabs 80 and 82 (FIG. 8). As the staple moves down into and through ejection slot 22, downward movement of tabs 78, 79, 80 and 82 is impeded by the edge portions of bottom wall 14 that define ejection slot 22, with the result that further downward action of ram plate 58 causes those tabs to be sheared off from the staple. In this shearing action, the center portion 59 of the bottom end of ram plate 58 that extends between lugs 62 acts as a shear blade against the edges of ejection slot 22.

FIGS. 13 and 14 help illustrate what happens as ram plate 58 continues advancing downward, pushing staple 70A ahead of it. In these figures, staple 70A is shown as it undergoes maximum deformation, which occurs just before it is sheared off from the magazine. As seen in FIG. 14, the staple is deformed under the action of push lugs 62 so that its legs 84 and 85 follow an arc of trajectory as they penetrate the tissue. This action, which is similar to the motion of a surgeon's suturing needle, is beneficial since it reduces the possibility and/or degree of stitching trauma. FIGS. 13 and 14 show staple 70A almost fully implanted, with the two edges of the incision drawn firmly and evenly together, since they are both under the control of the bottom wall 14 of hollow body 8.

FIGS. 15 and 16 illustrate the final or shearing action. The downward stroke of ram plate 58 is limited, stopping when portion 59 of its bottom end has passed a short distance below the upper surface of bottom wall 14 at ejection slot 22, that distance being far enough below bottom wall 14 to sever tabs 78, 79, 80 and 82 by the shearing action previously described. Since the thickness of ram plate 58 (its width is its horizontal dimension as seen in FIGS. 11, 13 and 15) is only slightly less than that of slot 22, there is virtually no space or gap remaining between those elements as the shearing of tabs 78, 79, 80 and 82 occurs. It is to be noted that as it pushes and shears off staple 70A, ram plate 58 actually depresses the tissue surface (see FIG. 16) so as to facilitate a substantially firm and flush alignment between the staple and the portions of the tissue that border on the incision.

The result is a solution long sought by surgeons. The two legs of staple 70A move in a true, or nearly true, circular arc about the pivot points represented by tabs 78, 79, 80 and 82 which are not yet sheared. As a consequence those tabs provide stable and positive pivot points (as seen in FIGS. 12, 14 and 16), with most of the penetration and pressure-forming of the staple under the force of ram plate 58 occurring while the staple is still attached firmly to the staple magazine.

The result is virtually absolute control of the implantation of the staple and a minimization of trauma caused by improper alignment and/or direction of the implanted staple. It is to be appreciated that the present stapler also provides excellent control over the depth of penetration of the staple.

It is to be noted that at the time of implantation of a staple 70, the staple is inelastically deflected downward by ram plate 58. When the staples 70 are finally sheared off from the magazine, they have already begun to pull upwardly from the tissue due to the edge-gathering forces resulting from their curving entry into the tissue. When a staple 70 is sheared off, its body or spine 83 will snap down against the surface of the tissue, thereby causing the staple to remain substantially flush with the tissue. When that occurs, the internal stresses imposed by the edge-gathering forces tend to disappear and incision 98 will remain perfectly closed but with a minimum of internal stresses and trauma.

The results and effects described above are obtained consistently and reliably with the present invention, in contrast with the great variability and uncertainty that characterizes present incision-closing techniques, especially those used in ophthalmology, where incision and suture sizes are extremely small and surgeons must depend on surgical microscopes for making and suturing incisions.

Turning now to FIGS. 1 and 17-20, there is shown a preferred form of driver 2 for operating the stapler described above. Driver 2 is designed to drive the staples with a velocity in excess of the ability of live tissues to react dynamically under the force of the penetrating staples, so as to make it unnecessary to hold and support the limp edges of some delicate tissues at the time of stapling.

Driver 2 comprises two hollow tubular bodies 102 and 104. Tubular body 102 is closed off at one end by an end wall 106 and has a reduced diameter forward end section 108 that is threaded as shown so that it may be screwed into a tapped hole in the adjacent end of second hollow body 104. Hollow body 102 has a constant diameter bore 112. Hollow body 104 has a forward end surface 115 and a reduced diameter hollow front extension 116. Hollow body 104 is characterized by a constant diameter axial bore 120 that extends from the forward end of its extension 116 and is transformed into four counterbores 121, 122, 123, and 124. The latter is threaded to mate with hollow body 102. Front extension 116 has an outer diameter such that it will make a snug sliding fit in counterbore 44 of the stapler head (FIG. 3), while bore 120 is sized so as to make a close sliding fit around the outer end 47 of ramrod 46.

The side wall of hollow body 104 is provided with an elongated flat-sided slot 128 for accommodating a clasp member 129. Slot 128 intersects forward end surface 115 and terminates a substantial distance short of the rear end surface 130 of hollow body 104 at a partition 131. Hollow body 104 has a second flat-sided slot 132 for accommodating a trigger member 133 and a trigger stop member 134. Slot 132 is located in diametric opposition to slot 128. Slot 132 extends from a point behind forward end surface 115 for approximately half the length of hollow body 104, and intersects counterbore 124. Hollow body 104 has a third slot 136 disposed in axial alignment with slot 128 for accommodating a pawl member 137. Slot 136 also intersects counterbore 124.

Disposed in bore 120 is a striker member 150. The latter has an enlarged head 152 having an outside diameter smaller than the diameters of counterbores 122 and 123. Surrounding striker member 150 is a compression spring 156 that urges the striker member toward counterbore 124. Spring 156 is engaged at one end with the shoulder formed by the junction of bore 120 and counterbore 121, while the opposite end of that spring engages head 152. Head 152 of striker 150 is engaged by the end of a ram member 160. Ram 160 has an enlarged head 162 at one end which engages a cylindrical inertia or weight member 166. The latter is engaged by a compression spring 170 that is disposed between weight 166 and the end wall 106, urging weight 166 away from end wall 106.

The forward end of ram 160 has a radially-extending finger 176 and an integral longitudinal extension 178, the latter being disposed eccentric to the center axis of the ram. Finger 176 has a catch 180 for engagement by a portion of pawl member 137, as hereinafter described. Ram extension 178 is notched as shown at 184 (FIG. 19) for engagement by a portion of trigger 133 as hereinafter described.

Figure 19:
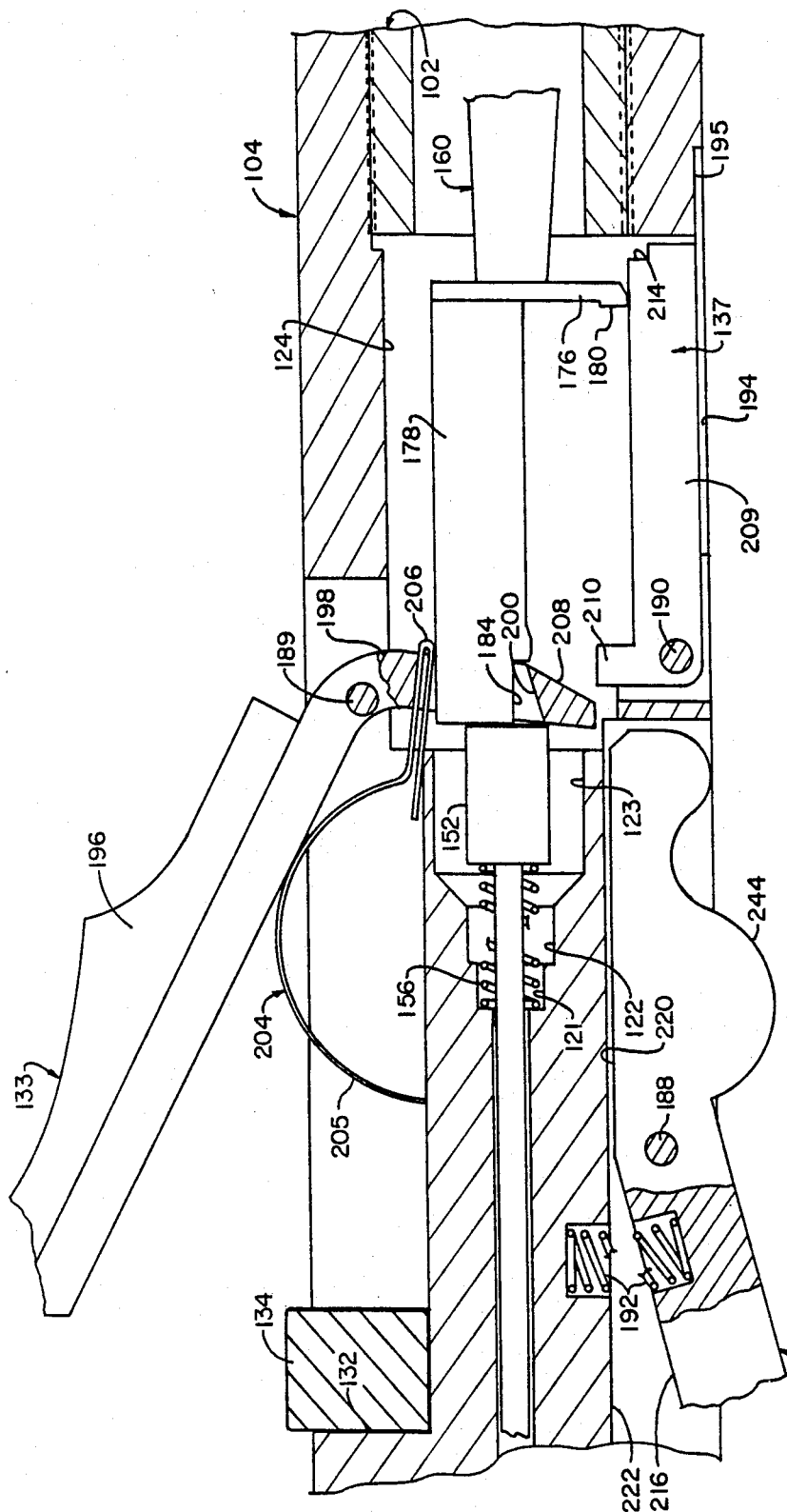
FIGS. 19 and 20 are enlarged fragmentary longitudinal views illustrating operation of the driver.
Figure 20:
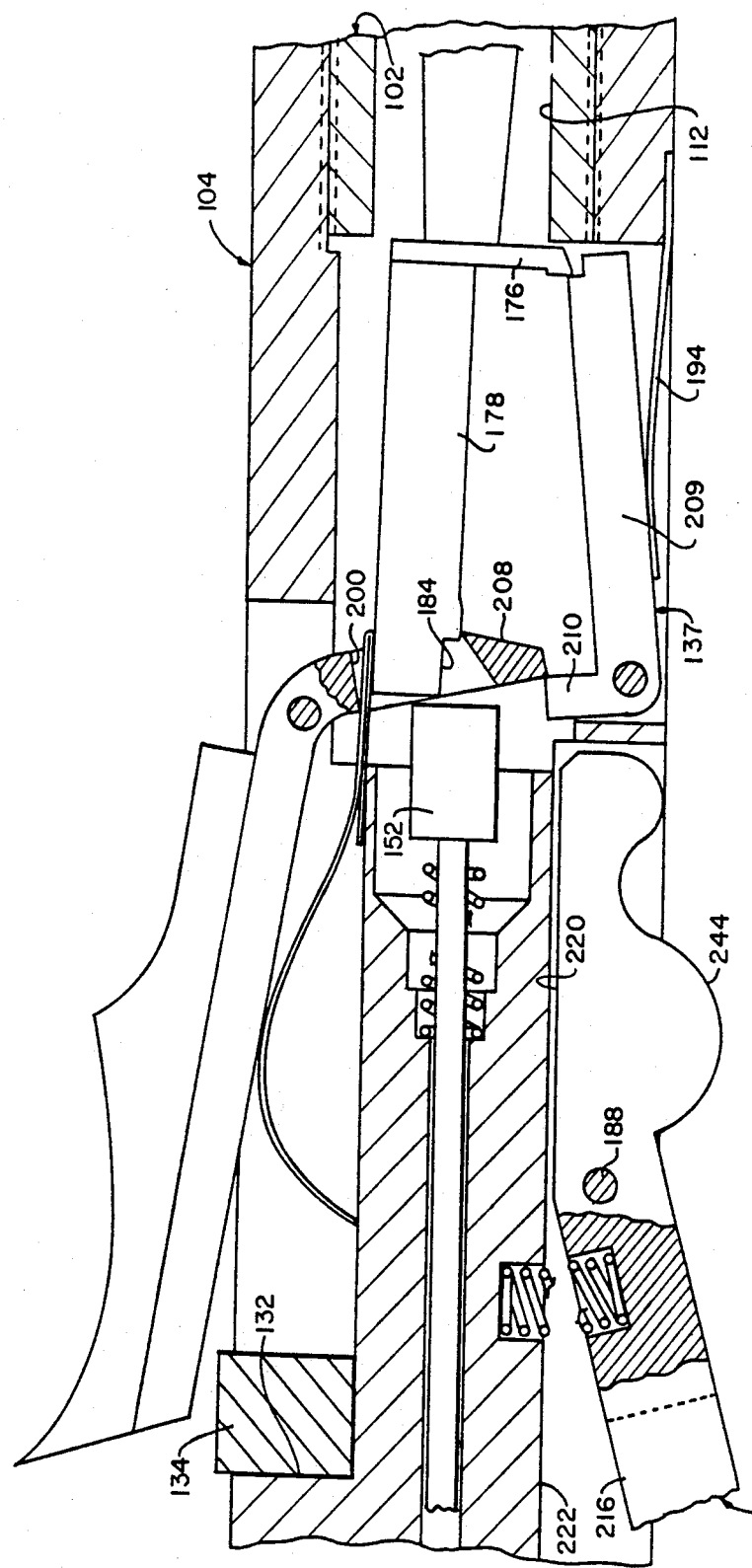

Clasp 129 is pivotally secured to hollow body 104 by a pivot pin 188 (FIG. 19), while trigger member 133 and pawl member 137 are pivotally attached to hollow body 104 by pivot pins 189 and 190, respectively. A compression spring 192, disposed in blind holes in clasp 129 and hollow body 104, urges the clasp to the open position shown in FIGS. 17, 19 and 20. Additionally a leaf spring 194 (FIG. 19) is brazed or welded in place in a shallow depression 195 in hollow body 104 that borders the slot 136. Leaf spring 194 bears against the long body portion 209 of pawl member 137 and urges it inwardly of the hollow body, i.e., so that it is urged in a counterclockwise direction as seen in FIGS. 17, 19 and 20.

Trigger 133 is generally L-shaped, comprising a first surgeon-engageable portion 196 and a ram actuating portion 198. Ram actuating portion 198 is provided with a hole 200 (FIG. 19) which is sized so as to make a loose fit with ram extension 178. A contoured leaf spring 204 has a first end portion 205 which engages the bottom of slot 132, and a folded back portion 206 which extends into hole 200 of trigger 133 and simultaneously engages the bottom surface of slot 132. The folded back portion 206 of spring 204 bears against the exterior surface of ram extension 178 so as to urge it downwardly (as viewed in FIGS. 17, 19 and 20) toward pivot pin 190. The ram engaging portion 198 of trigger 133 is provided with a bevelled surface 208 which faces finger 176.

Pawl member 137 comprises a long body portion 209 having a lateral extension 210 adjacent pivot pin 190. Lateral extension 210 extends adjacent to the bevelled surface 208 of trigger 133 when the latter and pawl member 137 are disposed in the driver's at-rest position shown in FIG. 19. Pawl member 137 also has a notch 214 at its free end for the purpose of making engagement with the catch portion of finger 176 when the driver is placed in cocking condition, as hereinafter described.

Clasp 129 has a surface 216 which extends at an angle to a surface 220, both of said surfaces being flat for engagement with the flat surface 222 that forms the bottom of slot 128. Engagement of surface 220 with surface 222 determines the open position of the clasp member, while engagement of surface 216 with surface 222 determines the closed position of the clasp member.

At its free or forward end clasp member 129 is provided with a right angle extension 228 (FIG. 17) and also is slotted as shown at 230 (FIGS. 17 and 18), whereby the forward end of the clasp member, including its right angle extension 228, is divided into two arms 234 and 236. The inner surfaces of arms 234 and 236 are contoured so as to have circularly curved confronting surfaces 238 and 240. The radius of curvature of each of the surfaces 238 and 240 is substantially the same as that of the exterior of surface 41 of socket-like member 40 (FIG. 2). Surfaces 234 and 236 extend far enough to be mutually converging where they intersect the flat end surfaces 239 of the free ends of the two arms, i.e., the end surfaces 239 of the free forward extremities of arms 234 and 236 are spaced from one another a distance less than the radius of curvature of surfaces 238 and 240.

The stapler head of FIGS. 1-10 is attached to the driver by inserting the driver's tubular extension 116 (FIG. 17) into axial counterbore 44 of the stapler's socket-like member 40 (FIG. 3). The socket-like member 40, its counterbore 4, striker 150 and extension 116 have lengths such that when extension 116 is inserted into socket-like member 40, striker 150 will lightly contact ramrod 46 and flange 43 will be spaced from end surface 115 of driver 2. Thereafter clasp 129 is pivoted clockwise as seen in FIG. 17, forcing its arms 234 and 236 to engage the circularly-curved outer surface 41 of the stapler head. Because arms 234 and 236 are resilient, under the pivoting force they will spring apart to pass around the reduced diameter section 41 of the stapler head. The resiliency of arms 234 and 236 then will automatically cause them to compress against outer surface 41, locking the stapler head to the driver. Removal of the stapler head from the driver is achieved by the operator's pressing of bump or projection 244 (FIG. 19), which in turn will cause clasp 129 to pivot counterclockwise (as viewed in FIGS. 17 and 19) out of contact with socket-like member 40.

Operation of the driver will now be described.

Assuming that the stapling head of FIGS. 1-10 is mounted on the front end of driver 2 and locked in place by clasp 129, the driver is cocked by depressing trigger 133 once, i.e., pivoting it counterclockwise as seen in FIG. 17, until it engages trigger stop member 134. As trigger 133 is depressed, its extension 198 engages the shoulder formed by notch 184 in ram extension 178 and forces ram member 160 to the right (as seen in FIGS. 17, 19 and 20), forcing inertia weight 166 to compress spring 170. Ram 160 is moved to the right far enough to position finger 176 beyond notch 214 in pawl 137, whereupon leaf spring 194 will force pawl 137 to pivot counterclockwise (as seen in FIG. 1) inwardly far enough for notch 214 of pawl 137 to engage catch 180 of ram member 160. Thereafter, when trigger 133 is released, spring 170 will urge ram member 160 to the left (as seen in FIG. 17), causing pawl 137 to pivot counterclockwise about its pivot pin 190 until extension 210 engages partition 131, whereupon ram 160 moves out of alignment with the internal oversized bore 112 of hollow body 102, unhooking trigger portion 198 from ram notch 184 (as used in this context, "out of alignment" means that the left hand end of ram member 160 is shifted upwardly in FIGS. 17, 19 and 20). At the same time, the free end of the portion 198 of trigger 133 will have intruded behind and be locked by the lateral extension 210 of pawl 137 (FIG. 20).

At this point the forward end of ram extension 178 may or may not be engaged by head 152 of striker 150, depending on the axial position of striker 150. In any case, it is to be appreciated that spring 156 does not actively bias striker head 152 against the retracted ram extension. See FIG. 20.

Firing of the cocked driver is achieved by depressing trigger 133 a second time. When this occurs, the lateral portion 198 of trigger 133 will force ram member 160 further out of alignment with the oversized bore 112 of hollow body 102, i.e., the extension 178 of ram member 160 is moved further upwardly against folded back portion 206 of spring 204 (as seen in FIGS. 17, 19 and 20), thereby disengaging catch 180 from the notched portion 214 of pawl member 137, whereupon the ram will be driven forward by inertia weight 166 acting under the force of spring 170. As a consequence, ram extension 178 will impact against head 152 of striker 150, driving the latter forward along bore 120. As it is propelled forward, striker 150 will engage ramrod 46 of the stapler head, causing the ramrod to drive ram plate 58 downwardly to cause a staple to be discharged in the manner previously described.

At the same time forward movement of ram member 160 will cause its finger 176 to slide along the inner surface of pawl 137, thereby camming pawl 137 in a clockwise direction (when viewed from the direction of FIGS. 17, 19 and 20) back to its original at-rest position, whereby on release of trigger 133 the trigger's lateral extension 198 is free to swing back to the position shown in FIGS. 17 and 19 without interference by the lateral extension 210 of pawl 137. At this point driver 2 is ready to be cocked again in preparation for implanting of another staple.

The driver shown in FIGS. 17-20 offers the advantage that it is compact, easy to hold and use, and can be arranged to cause ram plate 58 to drive staples 70 with a velocity substantially in excess of the ability of live tissues to react dynamically under the force of the penetrating staples, so as to make it unnecessary to hold together the limp edges of delicate tissues at the time of stapling. The latter advantage is very significant when using the stapling system to suture sensitive tissue, e.g. in ophthalmic or cosmetic surgery procedures. Further advantages are that the staples are positively positioned in line with ejection slot 22, thereby reducing the possibility of jamming or misfiring, and the stapler head is easily replaced by a new one when its supply of staples has been exhausted.

MODIFICATIONS OF THE PREFERRED EMBODIMENT

Obviously the apparatus herein described may be modified in various ways without departing from the essential principles of the invention. Thus the manner in which the driver is cocked and then fired may be modified by changing the shape and/or disposition of the lateral extension 198 of trigger 133, the forward end of ram member 160 and pawl 137. Similarly, the grip portion 196 of the trigger member may be changed so as to extend rearwardly rather than forwardly as shown. It also is contemplated that the mode of connection provided by clasp member 129 may be changed without affecting the mode of operation of the driver.

Figure 21:
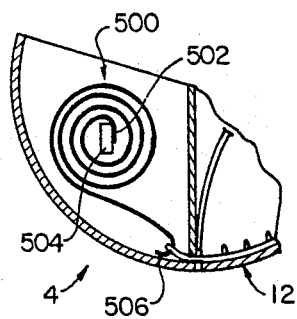
FIG. 21 is a partial side elevation, partly in section, illustrating an alternative form of stapler head.

Furthermore, the manner of advancing staple magazine 12 within stapler head 4 may be changed. Thus, for example, leaf spring 10 may be replaced by a coil spring 500 (FIG. 21) which has its interior end 502 attached to a crossbar 504 which extends between the stapler head's opposite side walls 16 and 18 (FIG. 2) and which has its exterior end 506 attached to the leading end of staple magazine 12.

It is also to be appreciated that the relative positions of spring 170 and weight 166 may be reversed, i.e., so that weight 166 engages end wall 106 and spring 170 engages the enlarged head 162 of ram 160. Such a construction will reduce the inertia to be overcome by spring 170 when driving ram 160 forward, thereby allowing the ram (and hence the staple) to be driven at a higher velocity.

Figure 9A:
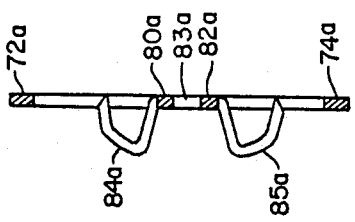
FIG. 9A is a sectional view of an alternative form of staple illustrating an alternative staple design.

It is also contemplated that the shape of the staples may be varied somewhat from that shown in FIG. 9. Thus, while the staples generally comprise a substantially straight body section and a pair of curved legs, it is possible to form the legs with something other than a "continuous" curvature. FIG. 9A illustrates such an alternative staple design. More specifically, the staple shown in FIG. 9A is identical to the staple shown in FIG. 9, except that each of the legs 84a, 85a of the staple of FIG. 9A is distinctly bent at two different points along the length of the leg, rather than being more or less "continuously" rounded as is the case with the legs of the staple of FIG. 9. The staple of FIG. 9A has been found to set itself flatter against certain types of body tissue than the staple of FIG. 9 in certain circumstances. It is to be appreciated that it is also possible to form the staple so that each of the legs of the staple is distinctly bent at only one point along the length of the leg, or is distinctly bent at more than two points along the length of the leg.

Still other changes will be obvious to persons skilled in the art without departing from the essential mode of operation of the invention.

What is claimed is:

1. In combination with a stapler head that has a reciprocally movable staple ram plate for separating a staple from a supply thereof and driving said staple into a selected workpiece,
    a stapler driver comprising:
    (a) reciprocally movable striker for engaging said staple ram plate and driving said staple ram plate in a first direction, (b) selectively operable means for causing said striker to move from a first retracted position to a second extended position so as to drive said staple ram plate in said first direction, and (c) return means for returning said striker from said second extended position to said first retracted position, said selectively operable means comprising:

(a) an elongated ram having a longitudinal axis, biasing means for urging said ram from a first retracted position to a second extended position, and trigger means for (a) moving said ram from said second extended position to said first position and thereafter maintaining said ram in said first retracted position when said trigger means in actuated a first time, and (b) moving at least a portion of said ram substantially perpendicularly to be longitudinal axis thereof so as to release said ram when said trigger means is actuated a second time so that said biasing means will move said ram from said first retracted position to said second extended position, whereby said ram will engage said striker and move it from its said first retracted position to its said second extended position.

2. A surgical stapling system according to claim 1 wherein said ram comprises a movable weight member for impacting said striker and causing said striker to impact and drive said staple ram plate.

3. A surgical stapling system according to claim 1 wherein said stapler driver is manually operated.

4. A surgical stapling system according to claim 1 wherein said staple driver is releasably attached to said stapler head.

5. A surgical stapling system according to claim 1 wherein said trigger means comprises a trigger assembly and a pawl assembly, said trigger assembly and said pawl assembly being adapted so that said trigger assembly will engage said ram and move it from its said second extended position to its said first retracted position wherein said trigger means is actuated a first time, whereupon said pawl assembly will engage and maintain said ram in said first retracted position, and said trigger assembly and said pawl assembly being adapted so that said trigger assembly will cause said pawl assembly to disengage from and release said ram when said trigger means is actuated a second time, whereupon said biasing means will cause said ram to move from its said first retracted position to its said second extended position.

6. A surgical stapling system according to claim 1 wherein said return means comprises a spring.

7. A surgical stapling system according to claim 1 wherein said biasing means comprises a spring.

8. A staple driver adapted for attachment a stapler head that includes (a) a magazine comprising a plurality of staples arranged in a series array, (b) a reciprocally movable member, and (c) a ram plate attached to said reciprocally movable member for dispensing said staples one at a time from said magazine in accordance with reciprocal movement of said reciprocally movable member, said staple drive comprising:

(a) reciprocally movable striker positioned for engagement with said reciprocally movable member and arranged so as to cause said reciprocally movable member to drive said ram plate in a first direction, (b) selectively operable means for causing said striker to move from a first retracted position to a second extended position so as cause said reciprocally movable member to drive said ram plate in said first direction, and (c) return means for returning said striker from said second extended position to said first retracted position.

said selectively operable means comprising:

an elongate ram having a longitudinal axis, biasing means for urging said ram from a first retracted position to a second extended position, and trigger means for (a) moving said ram from said second extended position to said first retracted position and thereafter maintaining said ram in said first retracted position when said trigger means is actuated a first time, and (b) moving at least a portion of said ram substantially perpendicularly to the longitudinal axis thereof so as to release said ram when said trigger means is actuated a second time so that said biasing means will move said ram from said first retracted position to said second extended position, whereby said ram will engage said striker and move it from its said first retracted position to its said second extended position.

9. A staple driver according to claim 8 wherein said driver comprises means for releasably attaching said driver to said stapler head.

10. A staple driver according to claim 9 comprising first and second body portions attached to one another, means for connecting said first body portion to said stapler head, and first and second axial bores in said first and second body portions respectively, said striker being slidably disposed in said first axial bore and being arranged to apply a driving force to said stapler head when said trigger means is actuated both first and second times.

11. A staple driver according to claim 8 wherein said trigger means comprises a trigger assembly having first means for moving said ram from said second extended position to said first retracted position when said trigger assembly is actuated a first time, second means for holding said ram in said first retracted position when said trigger means is actuated a first time, and third means for releasing said ram from said first retracted position and allowing it to be moved to said second extended position by said biasing means when said trigger means is actuated a second time.

12. A surgical stapling system according to claim 8 wherein said trigger means comprises a trigger assembly and a pawl assembly, said trigger assembly and said pawl assembly being adapted so that said trigger assembly will engage said ram and move it from its said second extended position to its said first retracted position when said trigger means is actuated a first time, whereupon said pawl assembly will engage and maintain said ram in said first retracted position, and said trigger assembly and said pawl assembly being adapted so that said trigger assembly will cause said pawl assembly to disengage from and release said ram when said trigger means is actuated a second time, whereupon said biasing means will cause said ram to move from its said first retracted position to its said second extended position.

13. A surgical stapling system according to claim 7 wherein said return means comprises a spring.

14. A surgical stapling system according to claim 8 wherein said biasing means comprises a spring.

* * * * *

UNITED STATES PATENT AND TRADEMARK OFFICE
CERTIFICATE OF CORRECTION

PATENT NO. : 4,821,942

DATED : April 18, 1989

INVENTOR(S) : William D. Richards, et al.

It is certified that error appears in the above-identified patent and that said Letters Patent is hereby corrected as shown below:

Claim 1, col. 10, line 65, the word "stapler" should be changed to the word -- staple --;

Claim 1, col. 11, line 9, the term "(a)" should be deleted;

Claim 1, col. 11, line 9, the word "elongated" should be changed to the word -- elongate --;

Claim 1, col. 11, line 13, the word -- retracted -- should be inserted after the word "first" and before the word "position";

Claim 1, col. 11, line 15, the word "in" should be changed to the word -- is --;

Claim 1, col. 11, line 17, the word "be" should be changed to the word -- the --;

Claim 3, col. 11, line 30, the word "stapler" should be changed to the word -- staple --;

Claim 5, col. 11, line 40, the word "wherein" should be changed to the word -- when --;

Claim 8, col. 11, line 54, the word -- to -- should be inserted after the word "attachment" and before the word "a";

Claim 8, col. 11, line 62, the word "drive" should be changed to the word -- driver --;

UNITED STATES PATENT AND TRADEMARK OFFICE
CERTIFICATE OF CORRECTION

PATENT NO. : 4,821,942

DATED : April 18, 1989

INVENTOR(S) : William D. Richards, et al.

It is certified that error appears in the above-identified patent and that said Letters Patent is hereby corrected as shown below:

Claim 8, col. 12, line 8, the period (.) should be changed to a comma (,); and

Claim 13, col. 12, line 64, the number "7" should be changed to the number -- 8 --.

Signed and Sealed this

Nineteenth Day of June, 1990

Attest:

HARRY F. MANBECK, JR.

Attesting Officer      Commissioner of Patents and Trademarks